(12) United States Patent
Plassman et al.

(10) Patent No.: US 9,119,564 B2
(45) Date of Patent: Sep. 1, 2015

(54) METHOD OF SIZING INTERNAL BODY STRUCTURE, AND MECHANISM AND SYSTEM FOR SAME

(71) Applicant: Cook Medical Technologies LLC, Bloomington, IN (US)

(72) Inventors: Trevor James Plassman, Bloomington, IN (US); Tyler Patrick Turk, Greenwood, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 243 days.

(21) Appl. No.: 13/944,303

(22) Filed: Jul. 17, 2013

(65) Prior Publication Data
US 2014/0073918 A1 Mar. 13, 2014

Related U.S. Application Data

(60) Provisional application No. 61/700,620, filed on Sep. 13, 2012.

(51) Int. Cl.
*G01B 13/10* (2006.01)
*A61B 5/107* (2006.01)
*A61B 5/00* (2006.01)
*A61B 6/00* (2006.01)
*E21B 47/08* (2012.01)
*G01B 5/12* (2006.01)

(52) U.S. Cl.
CPC ............ *A61B 5/1076* (2013.01); *A61B 5/6853* (2013.01); *E21B 47/08* (2013.01); *G01B 5/12* (2013.01); *G01B 13/10* (2013.01)

(58) Field of Classification Search
CPC ........... G01B 13/10; G01B 5/12; E21B 47/08
USPC ......................................... 33/543.1; 600/431
See application file for complete search history.

(56) References Cited

U.S. PATENT DOCUMENTS

| | | | |
|---|---|---|---|
| 3,038,259 A | 6/1962 | Smialowski et al. | |
| 4,995,878 A * | 2/1991 | Rai | 606/194 |
| 5,555,886 A | 9/1996 | Weng et al. | |
| 5,902,308 A * | 5/1999 | Murphy | 606/108 |
| 6,241,678 B1 * | 6/2001 | Afremov et al. | 600/481 |
| 7,476,203 B2 * | 1/2009 | DeVore et al. | 600/587 |
| 7,476,235 B2 * | 1/2009 | Diederich et al. | 606/192 |
| 7,738,626 B2 | 6/2010 | Weese et al. | |
| 7,856,730 B2 | 12/2010 | Sakai et al. | |
| 7,912,531 B1 * | 3/2011 | Chiu et al. | 600/423 |
| 8,083,692 B2 * | 12/2011 | Mangiardi et al. | 600/587 |
| 2003/0083690 A1 | 5/2003 | Bouchier | |
| 2004/0073108 A1 * | 4/2004 | Saeed et al. | 600/431 |
| 2006/0064039 A1 | 3/2006 | Griego et al. | |
| 2006/0155217 A1 | 7/2006 | DeVore et al. | |
| 2006/0167386 A1 | 7/2006 | Drake et al. | |
| 2009/0178289 A1 * | 7/2009 | Sakai et al. | 33/543.1 |
| 2010/0160832 A1 | 6/2010 | Braido | |
| 2011/0082392 A1 | 4/2011 | Mangiardi et al. | |
| 2012/0220909 A1 * | 8/2012 | Downing | 602/16 |

* cited by examiner

*Primary Examiner* — Laura Martin
*Assistant Examiner* — Rhyan C Lange
(74) *Attorney, Agent, or Firm* — Liell & McNeil

(57) ABSTRACT

Sizing an internal body structure in a patient includes guiding a sizing mechanism via a wire guide to a target location within the internal body structure, inflating a balloon of the sizing mechanism at the target location, and injecting a contrast fluid into the internal body structure. The inflated balloon blocks a flow of the injected contrast fluid to indicate that a size of the inflated balloon is accordant with a size of the body structure. Related apparatus is also disclosed.

20 Claims, 3 Drawing Sheets

METHOD OF SIZING INTERNAL BODY STRUCTURE, AND MECHANISM AND SYSTEM FOR SAME

RELATION TO OTHER PATENT APPLICATION

This application claims priority to provisional patent application 61/700,620, filed Sep. 13, 2012, with the same title.

TECHNICAL FIELD

The present disclosure relates generally to sizing an internal body structure in a patient, and relates more particularly to injecting contrast fluid into the internal body structure to indicate that a size of an inflated balloon of a sizing mechanism is accordant with a size of the body structure.

BACKGROUND

Many medical procedures require the size of a body structure in a patient to be determined. When a treatment device to be used internally relies for optimal functioning upon correct sizing to the body structure, measurement inaccuracies risk compromising treatment. Examples include embolization procedures where a vessel needs to be sized before delivering an occlusion device or the like, and procedures for the placement a stent or graft. Typical vessel sizing prior to performing a procedure includes first calibrating an imaging machine to the known size of a catheter tip, or a known distance between points on a sizing wire. A technician will then typically place two points on a screen of the imaging machine, one on each side of the vessel across the diameter of interest. The imaging machine will then compare the calibrated measurement to the current distance between the two points across the vessel to determine vessel diameter. A treating physician can then select a device to be placed within the vessel based upon the determined size.

The above general technique is of course subject to human error. For instance, if the two points placed on the screen are not placed exactly perpendicular to the width of the vessel, an inaccurate measurement may be taken. Another issue with standard techniques is that the imaging machine must be perfectly in plane, or nearly so, with the plane of the vessel at the measurement location. This can be very difficult to establish. If the imaging machine is not properly oriented, calibration may be inaccurate, and as a result so can the measurements taken. It also commonly takes ten minutes or even more to properly position and calibrate the machine, and measure the target vessel.

U.S. Pat. No. 7,856,730 B2 to Sakai et al. proposes an internal diameter measurement device that would appear to take some of the potential for human error out of vessel measurement. In Sakai et al., a tubular sheath is inserted into a body cavity, and a balloon provided on the distal end of the sheath is inflated to displace a linear reference member providing an indication of the internal diameter of the cavity. While the device of Sakai et al. may function adequately, it is not without shortcomings.

SUMMARY OF THE DISCLOSURE

In one aspect, a method of sizing an internal body structure in a patient includes guiding a sizing mechanism via a wire guide to a target location within the internal body structure, and inflating a balloon of the sizing mechanism at the target location via an inflation fluid. The method further includes injecting a contrast fluid into the internal body structure, and blocking a flow of the injected contrast fluid through the body structure at the target location via the inflated balloon, to indicate via an imaging mechanism that a size of the inflated balloon is accordant with a size of the body structure at the target location.

In another aspect, a mechanism for sizing an internal body structure in a patient includes an elongate body having a proximal body end and a distal body end, and defining a wire guide lumen for guiding the mechanism over a wire guide to a target location within the internal body structure. The mechanism further includes a balloon attached to the elongate body between the proximal and distal body ends, and the elongate body further defining an inflation fluid lumen configured to connect with a supply of inflation fluid and being in fluid communication with the balloon, for inflating the balloon at the target location. The elongate body further defines a contrast injection lumen configured to connect with a supply of contrast fluid, and having an outlet located proximal to the balloon, for injecting the contrast fluid into the internal body structure to indicate that a size of the inflated balloon is accordant with a size of the body structure at the target location.

In still another aspect, a system for sizing an internal body structure in a patient includes a supply of inflation fluid, a supply of contrast fluid, and a sizing mechanism. The sizing mechanism includes an elongate body having a proximal body end and a distal body end, and a balloon attached to the elongate body between the proximal body end and the distal body end. The elongate body defines a wire guide lumen, an inflation fluid lumen fluidly connected with the supply of inflation fluid, and a contrast injection lumen fluidly connected with the supply of contrast fluid. The inflation fluid lumen is in fluid communication with the balloon, for inflating the balloon at the target location. The contrast injection lumen has an outlet located proximal to the balloon, for injecting the contrast fluid into the internal body structure to indicate that a size of the inflated balloon is accordant with a size of the body structure at the target location.

DETAILED DESCRIPTION

Figure 1:
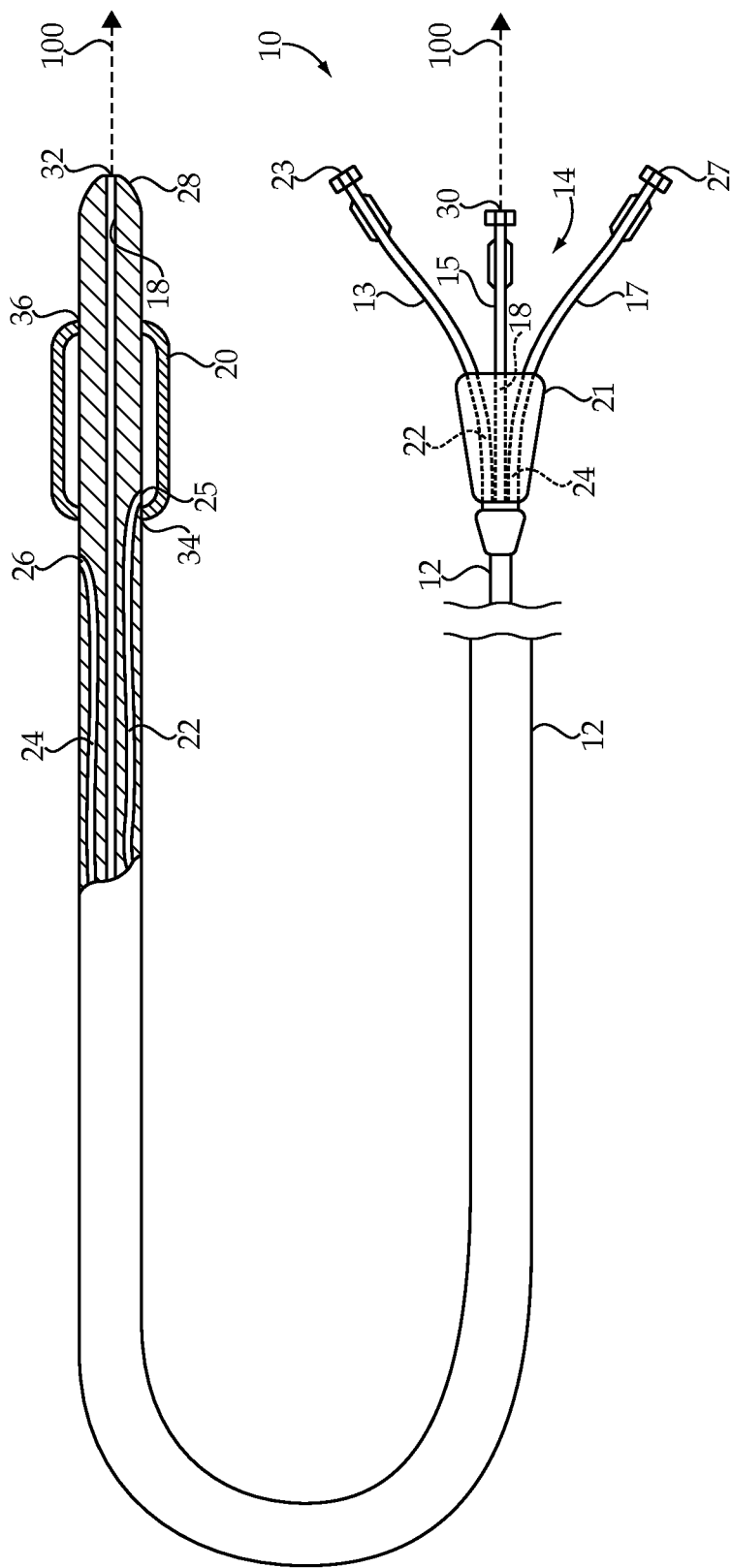
FIG. 1 is a partially sectioned side diagrammatic view of a mechanism for sizing an internal body structure in a patient, according to one embodiment.

Referring to FIG. 1, there is shown a mechanism 10 for sizing an internal body structure in a patient. Mechanism 10 includes an elongate tubular body 12 defining a longitudinal axis 100 and having a proximal body end 14, and a distal body end 16. Elongate body 12 defines a wire guide lumen 18 for guiding mechanism 10 over a wire guide to a target location within an internal body structure. A balloon 20 is attached to elongate body 12 between proximal body end 14 and distal body end 16. Elongate body 12 further defines an inflation fluid lumen 22 configured to connect with a supply of inflation fluid and in fluid communication with balloon 20, for inflating balloon 20 at the target location. Elongate body 12 further defines a contrast injection lumen 24 configured to connect with a supply of contrast fluid. Wire guide lumen 18 extends between a first wire guide opening 30 formed in proximal body end 14, and a second wire guide opening 32 formed in distal body end 16. Lumen 22 extends between an inlet 23 formed in proximal body end 14, and an outlet 25 communicating with an interior of balloon 20. Lumen 24 extends between an inlet 27 formed in proximal body end 14, and an outlet 26 located proximal to balloon 20, for injecting the contrast fluid into the internal body structure to indicate that a size of the inflated balloon is accordant with a size of the body structure at the target location, in a manner further described herein. In a practical implementation strategy, proximal body end 14 includes a plurality of leader tubes, in particular a first leader tube 13 providing fluid communication between inlet 23 and lumen 22, a second leader tube 15 providing fluid communication between wire guide opening 30 and lumen 18, and a third leader tube 17 providing fluid communication between inlet 27 and lumen 24. A manifold 21 is provided to connect the leader tubes with a more distal part of elongate body 12 in the embodiment pictured in FIG. 1.

Elongate body 12 further includes a distal tip 28 which may have wire guide opening 32 formed therein. As measured in an axial direction between manifold 21 and distal tip 28 within elongate body 12, lumen 18 may have a longer length, lumen 24 a shorter length, and lumen 22 a medium length. Elongate body 12 may include a one-piece elongate body, however, the present disclosure is not thereby limited. Balloon 20 may be circumferential of elongate body 12, and has a proximal balloon end 34 sealingly attached to elongate body 12 at a first location, and a distal balloon end 36 sealingly attached to elongate body 12 at a second location proximal to distal tip 28, as shown in FIG. 1.

Figure 2:
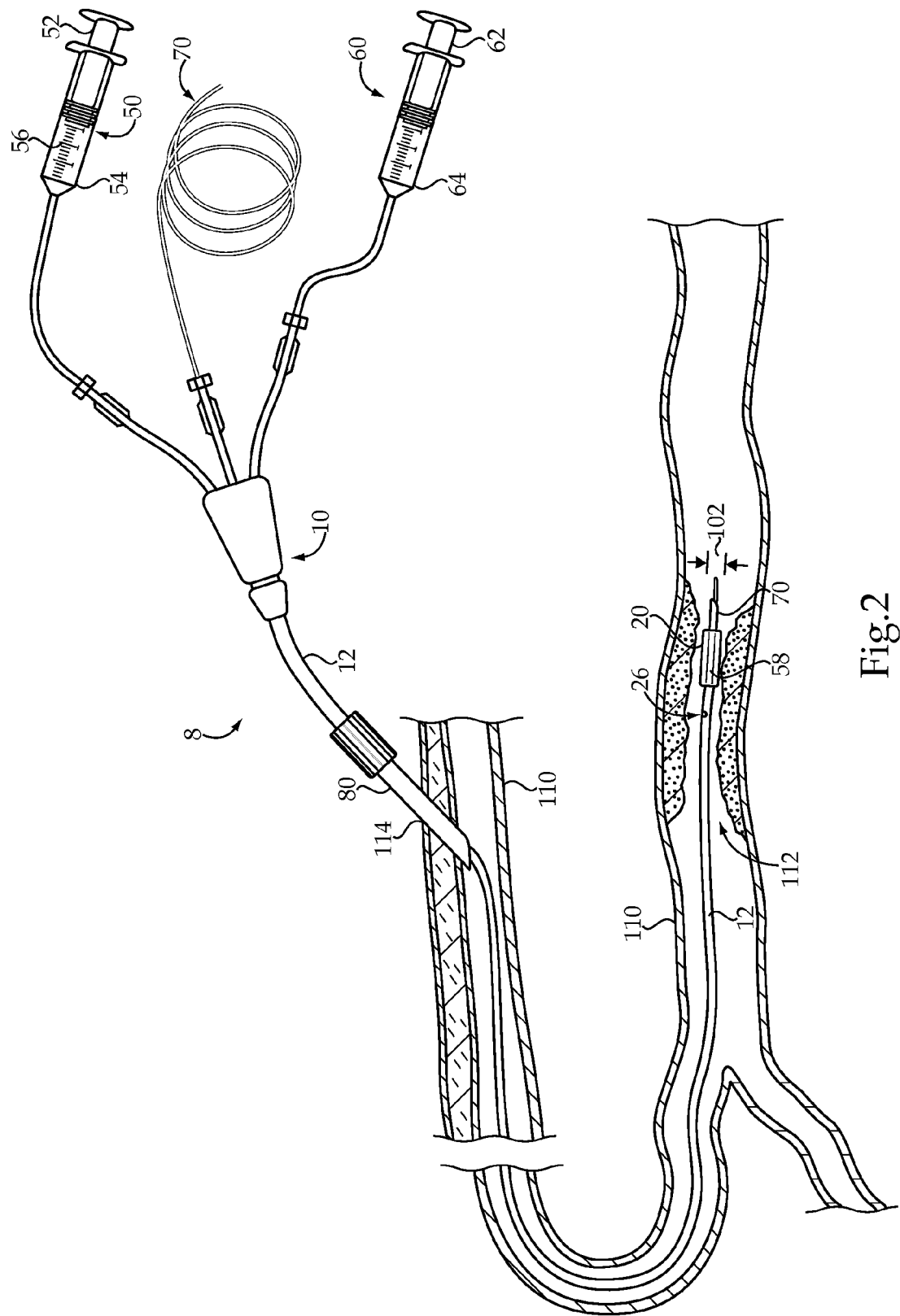
FIG. 2 is a side diagrammatic view of a system for sizing an internal body structure at one stage of a sizing procedure, according to one embodiment.

Referring also now to FIG. 2, there is shown mechanism 10 incorporated in a system 8 for sizing an internal body structure in a patient. System 8 may also include a supply of inflation fluid 50 connected with lumen 22, a supply of contrast fluid 60 connected with lumen 24, and a wire guide 70. The inflation fluid might include saline or contrast fluid, and the contrast fluid may include any suitable biocompatible contrast agent, typically a liquid. In FIG. 2, system 8 is shown as it might appear where mechanism 10 has been advanced by way of an introducer 80 through an opening 114 formed in the patient's skin, to percutaneously access an internal body structure 110 of the patient. Mechanism 10 has been advanced over wire guide 70 to a target location 112 within body structure 110. Body structure 110 may include a vessel such as a vein or artery, and target location 112 may be a stenosis or other constriction, however, the present disclosure is not thereby limited. In other embodiments, internal body structure 110 might include an otherwise healthy, unobstructed vessel supplying blood to a downstream area to be treated. In the former case, a stenosis or the like, mechanism 10 may be used in system 8 to size an internal diameter dimension at target location 112 for placement of an appropriately sized stent, for example. In the latter case, the vessel might be sized for the placement of an embolization device such that blood flow to a downstream tumor can be blocked, for purposes which will be readily apparent to those skilled in the art.

In any event, in the embodiment shown inflation fluid supply 50 contains the inflation fluid within a housing 54 having a movable plunger 52 positioned therein. Markings 56 are placed on housing 54 to enable a clinician to determine a volume of inflation fluid injected to inflate balloon 20. Supply 50 may thus be understood to include a metering device enabling a clinician to incrementally inflate balloon 20 via metered amounts of inflation fluid, the significance of which will be apparent from the following description. Fluid supply 60 may be analogously configured with a housing 64 and a plunger 62, and capable of metering injections of contrast fluid contained within housing 64.

In the state depicted in FIG. 2, balloon 20 is in an uninflated rest state and will be understood to define a first volume. Balloon 20 is inflatable to a plurality of working states having a plurality of different volumes defining a sizing range of mechanism 10. In the rest state, balloon 20 includes a plurality of longitudinal folds 58. As will be understood by way of the subsequently described drawings, balloon 20 may be free from folds in each of the plurality of working states. Balloon 20 may include a compliant or semi-compliant balloon in a practical implementation strategy, formed of latex or polyurethane, for example, such that balloon 20 may be inflated and conform to a size and shape of the body structure to be sized, in a manner further discussed herein. These features contrast with non-compliant balloons such as those used in angioplasty, and configured to deform a vessel via inflation.

To this end, balloon 20 may be elastically deformable between the rest state, approximately as shown in FIG. 2, and each of the plurality of working states. Balloon 20 may be plastically deformable upon inflation to or above a failure volume defining an upper end of the sizing range. Balloon 20 has a first volume in the rest state as noted above, and the failure volume may be greater than the first volume by a factor of about 1 to about 6. Another way to understand these structural properties of balloon 20 is that it may be inflated and increased in volume from about 1 to about 6 times the volume of its rest state, and will tend to return to the same rest state volume as well as rest state shape, when deflated. Where balloon 20 is inflated to or above the failure volume, however, balloon 20 will typically have a tendency to deform, such that when deflated balloon 20 will no longer return to the same rest state volume and/or shape. The sizing range of balloon 20 may be a range of a few millimeters. For example, balloon 20 may be configured for sizing vessels from about 2 millimeters to about 4 millimeters, from about 4 millimeters to about 6 millimeters, from about 6 millimeters to about 8 millimeters, and so on. In FIG. 2, balloon 20 defines a first outer diameter dimension 102 which is less than an inner diameter dimension of body structure 110 at target location 112.

INDUSTRIAL APPLICABILITY

With continued reference to FIGS. 1 and 2, as noted above mechanism 10 may be guided via sliding over wire guide 70 in a proximal to distal direction to target location 112 within body structure 110. With balloon 20 appropriately positioned, it may be inflated at target location 112 via the inflation fluid to initiate the process of sizing body structure 110. In a practical implementation strategy, an iterative process of incrementally injecting the contrast fluid into body structure 110, and incrementally inflating balloon 20. This procedure may be used to indicate when balloon 20 has been inflated to a state at which it blocks a flow of injected contrast fluid through body structure 110 via formation of a seal between balloon 20 and an inner wall of body structure 110. Injection of contrast and inflation fluid may occur simultaneously, and in an incremental, stepwise fashion. In conjunction with contrast fluid injection, forming the seal provides an indication that can be observed on an imaging screen that a size of balloon 20 is accordant with a size of body structure 110 at target location 112. As noted above, the size of balloon 20 may include an outer diameter dimension, as measured in a direction normal to axis 100. The size of the body structure may include an inner diameter dimension in the same frame of reference, and defined by the inner wall of body structure 110.

Figure 3:
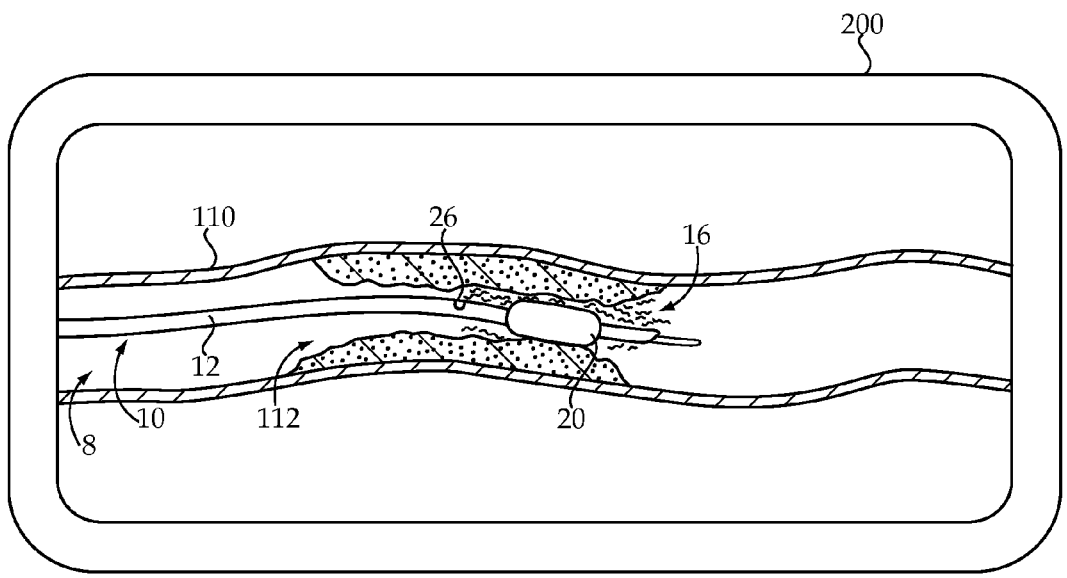
FIG. 3 is a side diagrammatic view of a portion of the system of FIG. 2, at another stage of the procedure.

Referring also now to FIG. 3, there is shown mechanism 10 where balloon 20 has been inflated to a working state but has not yet formed a seal with internal body structure 110. In FIG. 3, mechanism 10 is shown within body structure 110 as imaged via an imaging device display 200, although those skilled in the art will appreciate that on actual image would in practice likely appear different from what is shown in FIG. 3. Accordingly, injected contrast fluid 116 flows through body structure 110 past balloon 20. A clinician can thus determine on an imaging screen that balloon 20 is partially inflated, since contrast fluid 116 flows past balloon 20, and that the size of balloon 20 is not yet accordant with the size of body structure 110. In FIG. 3, the injection of contrast fluid may be understood as occurring at an earlier time.

Figure 4:
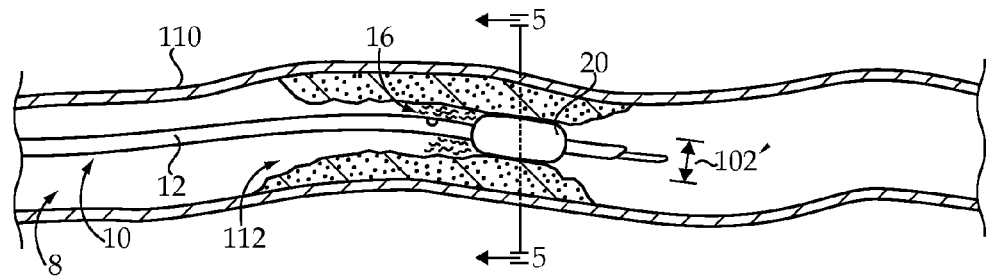
FIG. 4 is a side diagrammatic view of a portion of the system of FIG. 2 at yet another stage of the procedure.

Referring also now to FIG. 4, there is shown mechanism 10 as it might appear where balloon 20 has been further inflated to a working state at which it blocks flow of contrast fluid 116 through body structure 110. At the state depicted in FIG. 4, a clinician can thus determine that a seal between balloon 20 and the inner wall of body structure 110 has formed, thereby providing an indication that the size of balloon 20, in the illustrated case an expanded outer diameter dimension 102', is now accordant with the size of body structure 110. While only two increments of balloon inflation and contrast fluid injection are depicted in FIGS. 3 and 4, it will be appreciated that a greater number of incremental inflations and incremental injections of contrast fluid might be used to gradually transition from the state of mechanism 10 depicted in FIG. 2 to the state depicted in FIG. 4.

Since inflation fluid supply 50 allows a clinician to meter a volume of inflation fluid, it can readily be determined how much inflation fluid has been used to inflate balloon 20 to the state shown in FIG. 4. And, since a volume of inflation fluid used is correlated with a size of balloon 20, the clinician can readily determine the size of the body structure 110 at target location 112. Another way to understand these principles is that metering the inflation fluid into the balloon provides an indication of a volume of the inflation fluid that corresponds with a size of balloon 20 once inflated to the state accordant with the size of the body structure. Inflation fluid volumes and corresponding balloon sizes are readily empirically determinable. It is contemplated that a chart or the like listing inflation fluid volumes in comparison with balloon outer diameter dimensions may be provided for reference by the clinician. With the size of the body structure now known, typically an internal diameter dimension, a suitable treatment device may then be obtained. As noted above, the treatment device might include a stent or an embolization device, or still another type of treatment device such as a graft. Injection of the contrast fluid may include a greater amount at an earlier time such as that shown in FIG. 3, and a lesser amount at a later time such as that shown in FIG. 4. Injecting a decreasing amount of the contrast fluid as balloon 20 gets closer and closer to a size at which it will form the seal with body structure 110 can minimize the injection of contrast fluid interfering with the seal formation, and thus ensure that sizing is as accurate as practicable. In a practical implementation strategy, an amount of contrast fluid injected may be reduced generally inversely proportional to an inflation state of balloon 20. Accordingly, when balloon 20 is uninflated a first amount of contrast fluid may be injected. When balloon 20 is approximately half-way inflated, having a diameter approximately one-half an internal diameter of body structure 110, an injection of contrast fluid may be about one-half the first amount, and so on.

Figure 5:
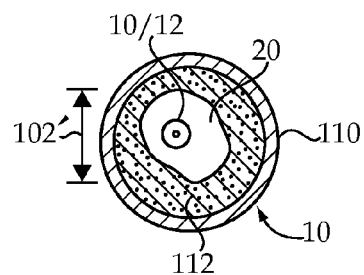
FIG. 5 is a sectioned view taken along line 5-5 of FIG. 4.

Turning to FIG. 5, there is shown a sectioned view along line 5-5 of FIG. 4. It may be noted that balloon 20 has assumed a noncircular shape and has thus conformed in both shape and size to a shape and size of internal body structure 110 at target location 112. Those skilled in the art will appreciate that, depending upon the shape of the internal body structure being sized at the target location, slightly different volumes of inflation fluid might be required to inflate the balloon to a state blocking flow of the contrast fluid. In other words, a first volume of inflation fluid might be required to inflate balloon 20 to size "x" where conforming to a vessel of one shape. A slightly different volume of inflation fluid might be used to inflate balloon 20 to size "x" where conforming to a vessel of a different shape. This potential for error is nevertheless considered to be sufficiently small to enable a clinician to determine the general size range of an interventional device to be placed within the body structure. In other words, since many interventional devices are configured for use within body structures of a certain size range, mechanism 10 is contemplated to more than adequately indicate the size range of the body structure despite minor volumetric deviations which could occur based upon the shape of the body structure being sized.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. For instance, rather than injecting contrast fluid at a location proximal to balloon 20, contrast fluid might be injected through wire guide lumen 18. In the illustrated embodiment, flow of blood through body structure 110 will generally be in a left to right direction, thus flow of the blood will tend to carry injected contrast fluid past balloon 20 in a left to right direction until balloon 20 forms a seal with body structure 110 as described herein. Where mechanism 10 is advanced into body structure 110 in a direction counter to blood flow, injection of contrast fluid upstream of balloon 120, e.g. through lumen 18, may thus be employed. It should also be appreciated that lumen 18 might be used to itself provide a passage for the placement of a treatment device. In other words, mechanism 10 might be used both to size an internal body structure and to provide for accessing the target location within the body structure for placement of a stent, embolization device, etc. Other aspects, features and advantages will be apparent upon an examination of the attached drawings and appended claims.

What is claimed is:

1. A method of sizing an internal body structure in a patient comprising the steps of:
   guiding a sizing mechanism via a wire guide to a target location within the internal body structure;
   inflating a balloon of the sizing mechanism at the target location via an inflation fluid;
   injecting a contrast fluid into the internal body structure; and
   blocking a flow of the injected contrast fluid through the body structure at the target location via the inflated balloon, to indicate via an imaging device that a size of the inflated balloon is accordant with a size of the body structure at the target location.

2. The method of claim 1 wherein the step of guiding includes sliding a one-piece elongate body of the sizing mechanism attached to the balloon in a proximal to distal direction over the wire guide.

3. The method of claim 2 wherein the step of injecting includes injecting the contrast fluid from the one-piece elongate body into the body structure at a location proximal to the balloon.

4. The method of claim 1 wherein the size of the inflated balloon includes an outer diameter dimension, and the size of the body structure includes an inner diameter dimension defined by an inner wall of the body structure.

5. The method of claim 3 further comprising a step of forming a seal between the balloon and the inner wall via the inflating of the balloon.

6. The method of claim 5 wherein the step of forming a seal further includes forming the seal via conforming a shape of the balloon to a non-circular shape defined by the inner wall of the body structure.

7. The method of claim 5 wherein the step of injecting further includes injecting the contrast fluid at a later time, and further comprising a step of injecting contrast fluid at an earlier time.

8. The method of claim 7 wherein the step of injecting contrast fluid at an earlier time includes injecting the contrast fluid prior to the forming of the seal, such that the contrast fluid flows past the balloon to indicate the size of the balloon is not accordant with the size of the body structure.

9. The method of claim 8 wherein the later injection includes a lesser amount of the contrast fluid, and the earlier injection includes a greater amount of the contrast fluid.

10. The method of claim 1 wherein the step of inflating further includes incrementally inflating the balloon, and the step of injecting further includes incrementally injecting the contrast fluid.

11. The method of claim 10 wherein incrementally inflating the balloon includes metering the inflation fluid into the balloon to provide an indication of a volume of the inflation fluid that corresponds with the size of the inflated balloon when accordant with the size of the body structure.

12. The method of claim 11 wherein the body structure includes a vein or artery, and wherein the step of guiding further includes sliding the sizing mechanism over the wire guide through a percutaneous opening into the vein or artery.

13. A mechanism for sizing an internal body structure in a patient comprising:
an elongate body including a proximal body end and a distal body end, and defining a wire guide lumen for guiding the mechanism over a wire guide to a target location within the internal body structure;
a balloon attached to the elongate body between the proximal and distal body ends, and the elongate body further defining an inflation fluid lumen configured to connect with a supply of inflation fluid and being in fluid communication with the balloon, for inflating the balloon at the target location; and
the elongate body further defining a contrast injection lumen configured to connect with a supply of contrast fluid, and having an outlet located proximal to the balloon, for injecting the contrast fluid into the internal body structure to indicate that a size of the inflated balloon is accordant with a size of the body structure at the target location.

14. The mechanism of claim 13 wherein the elongate body further includes a distal tip, and the wire guide lumen extends through the elongate body between a first wire guide opening formed in the proximal body end, and a second wire guide opening formed in the distal tip.

15. The mechanism of claim 14 wherein the elongate body includes an elongate one-piece body, and wherein the wire guide lumen has a longer length, the contrast injection lumen has a shorter length, and the inflation fluid lumen has a medium length, within the elongate one-piece body.

16. The mechanism of claim 15 wherein the balloon is circumferential of the elongate body and has a proximal balloon end attached to the elongate body at a first location, and a distal balloon end attached to the elongate body at a second location proximal to the distal tip.

17. The mechanism of claim 13 wherein:
the balloon is in an uninflated rest state, and is inflatable to a plurality of working states having a plurality of different volumes defining a sizing range of the sizing mechanism; and
the balloon includes a plurality of folds in the rest state, and is free from folds in each of the plurality of working states.

18. The mechanism of claim 17 wherein:
the balloon is elastically deformable between the rest state and each of the plurality of working states, and plastically deformable upon inflation to or above a failure volume defining an upper end of the sizing range; and
the balloon has a first volume in the rest state, and the failure volume is greater than the first volume by a factor of about one to about six.

19. A system for sizing an internal body structure in a patient comprising:
a supply of inflation fluid;
a supply of contrast fluid;
a sizing mechanism including an elongate body having a proximal body end and a distal body end, and a balloon attached to the elongate body between the proximal body end and the distal body end;
the elongate body defining a wire guide lumen, an inflation fluid lumen fluidly connected with the supply of inflation fluid, and a contrast injection lumen fluidly connected with the supply of contrast fluid; and
the inflation fluid lumen being in fluid communication with the balloon, for inflating the balloon at the target location, and the contrast injection lumen having an outlet located proximal to the balloon, for injecting the contrast fluid into the internal body structure to indicate that a size of the inflated balloon is accordant with a size of the body structure at the target location.

20. The system of claim 19 wherein the elongate body includes an elongate one-piece body, and wherein the wire guide, inflation fluid, and contrast injection lumens have longer, medium, and shorter lengths, respectively, within the elongate one-piece body, and further comprising a wire guide positioned within the wire guide lumen and extending through the elongate one-piece body.

* * * * *